United States Patent
Salo

(10) Patent No.: US 9,155,896 B2
(45) Date of Patent: Oct. 13, 2015

(54) METHOD AND APPARATUS FOR IMPROVING CARDIAC EFFICIENCY BASED ON MYOCARDIAL OXYGEN CONSUMPTION

(75) Inventor: Rodney Salo, Fridley, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 2030 days.

(21) Appl. No.: 11/316,123

(22) Filed: Dec. 22, 2005

(65) Prior Publication Data

US 2007/0150017 A1 Jun. 28, 2007

(51) Int. Cl.
*A61N 1/00* (2006.01)
*A61B 5/04* (2006.01)
*A61N 1/362* (2006.01)
*A61N 1/365* (2006.01)

(52) U.S. Cl.
CPC .......... *A61N 1/3627* (2013.01); *A61N 1/36557* (2013.01)

(58) Field of Classification Search
USPC ..................................... 600/323–324; 607/28
See application file for complete search history.

(56) References Cited

U.S. PATENT DOCUMENTS

| | | | |
|---|---|---|---|
| 4,436,092 A * | 3/1984 | Cook et al. .................. 607/21 |
| 4,543,954 A * | 10/1985 | Cook et al. .................. 607/21 |
| 4,726,383 A * | 2/1988 | Cook et al. .................. 607/21 |
| 4,791,935 A | 12/1988 | Baudino et al. |
| 4,807,629 A | 2/1989 | Baudino et al. |
| 4,813,421 A | 3/1989 | Baudino et al. |
| 4,830,488 A | 5/1989 | Heinze et al. |
| 4,928,688 A | 5/1990 | Mower |
| 4,995,390 A * | 2/1991 | Cook et al. .................. 607/21 |
| 5,058,584 A | 10/1991 | Bourgeois |
| 5,081,988 A * | 1/1992 | Cook et al. .................. 607/21 |
| 5,085,215 A * | 2/1992 | Nappholz et al. ........... 607/17 |
| 5,133,349 A * | 7/1992 | Heinze ....................... 607/22 |
| 5,213,098 A * | 5/1993 | Bennett et al. .............. 607/18 |
| 5,334,222 A | 8/1994 | Salo |
| 5,342,406 A | 8/1994 | Thompson |
| 5,435,308 A * | 7/1995 | Gallup et al. ............. 600/342 |
| 5,776,060 A | 7/1998 | Smith |
| 5,891,176 A * | 4/1999 | Bornzin ...................... 607/18 |
| 6,026,320 A | 2/2000 | Carlson |
| 6,094,591 A * | 7/2000 | Foltz et al. ................ 600/419 |
| 6,221,011 B1 | 4/2001 | Bardy |
| 6,270,457 B1 | 8/2001 | Bardy |
| 6,275,727 B1 | 8/2001 | Hopper et al. |
| 6,277,072 B1 | 8/2001 | Bardy |
| 6,280,380 B1 | 8/2001 | Bardy |
| 6,280,389 B1 | 8/2001 | Ding |

(Continued)

FOREIGN PATENT DOCUMENTS

| | | | | |
|---|---|---|---|---|
| DE | 3234388 A1 * | 4/1984 | ............ G01N 33/48 |
| EP | 261787 A1 * | 3/1988 | ............ A61B 5/00 |

(Continued)

*Primary Examiner* — Nicole F Lavert
(74) *Attorney, Agent, or Firm* — Schwegman Lundberg & Woessner, P.A.

(57) ABSTRACT

Devices and methods for improving cardiac efficiency involve measuring, patient-internally, an oxygen saturation parameter indicative of oxygen usage of myocardial tissue of the heart. A cardiac electrical therapy is adjusted to cause a change of the measured oxygen saturation parameter, and the adjusted cardiac electrical therapy is selected for delivery based on a changed oxygen saturation parameter indicative of an increase in cardiac efficiency.

19 Claims, 6 Drawing Sheets

(56) References Cited

U.S. PATENT DOCUMENTS

| | | |
|---|---|---|
| 6,285,907 B1 | 9/2001 | Kramer |
| 6,312,378 B1 | 11/2001 | Bardy |
| 6,336,903 B1 | 1/2002 | Bardy |
| 6,358,203 B2 | 3/2002 | Bardy |
| 6,368,284 B1 | 4/2002 | Bardy |
| 6,371,922 B1 | 4/2002 | Baumann |
| 6,398,728 B1 | 6/2002 | Bardy |
| 6,400,973 B1 * | 6/2002 | Winter ............ 600/323 |
| 6,411,848 B2 | 6/2002 | Kramer |
| 6,424,865 B1 | 7/2002 | Ding |
| 6,440,066 B1 | 8/2002 | Bardy |
| 6,459,929 B1 | 10/2002 | Hopper |
| 6,542,775 B2 | 4/2003 | Ding |
| 6,597,951 B2 | 7/2003 | Kramer |
| 6,645,153 B2 * | 11/2003 | Kroll et al. ............ 600/481 |
| 6,666,826 B2 * | 12/2003 | Salo et al. ............ 600/485 |
| 7,467,012 B1 * | 12/2008 | Park et al. ............ 607/20 |
| 2002/0151936 A1 | 10/2002 | Kloss et al. |
| 2003/0009199 A1 * | 1/2003 | Reinke et al. ............ 607/17 |
| 2003/0130702 A1 | 7/2003 | Kramer |
| 2003/0199956 A1 * | 10/2003 | Struble et al. ............ 607/122 |
| 2004/0220629 A1 | 11/2004 | Kamath |
| 2005/0124872 A1 | 6/2005 | Gutierrez |

FOREIGN PATENT DOCUMENTS

| | | | |
|---|---|---|---|
| EP | 271340 A1 * | 6/1988 | ........ A61B 5/00 |
| EP | 290273 A1 * | 11/1988 | ........ A61B 5/00 |
| WO | WO 93/02745 | 2/1993 | |
| WO | WO 97/43001 | 11/1997 | |
| WO | WO 01/58518 | 8/2001 | |
| WO | WO 2005/046790 | 5/2005 | |

* cited by examiner

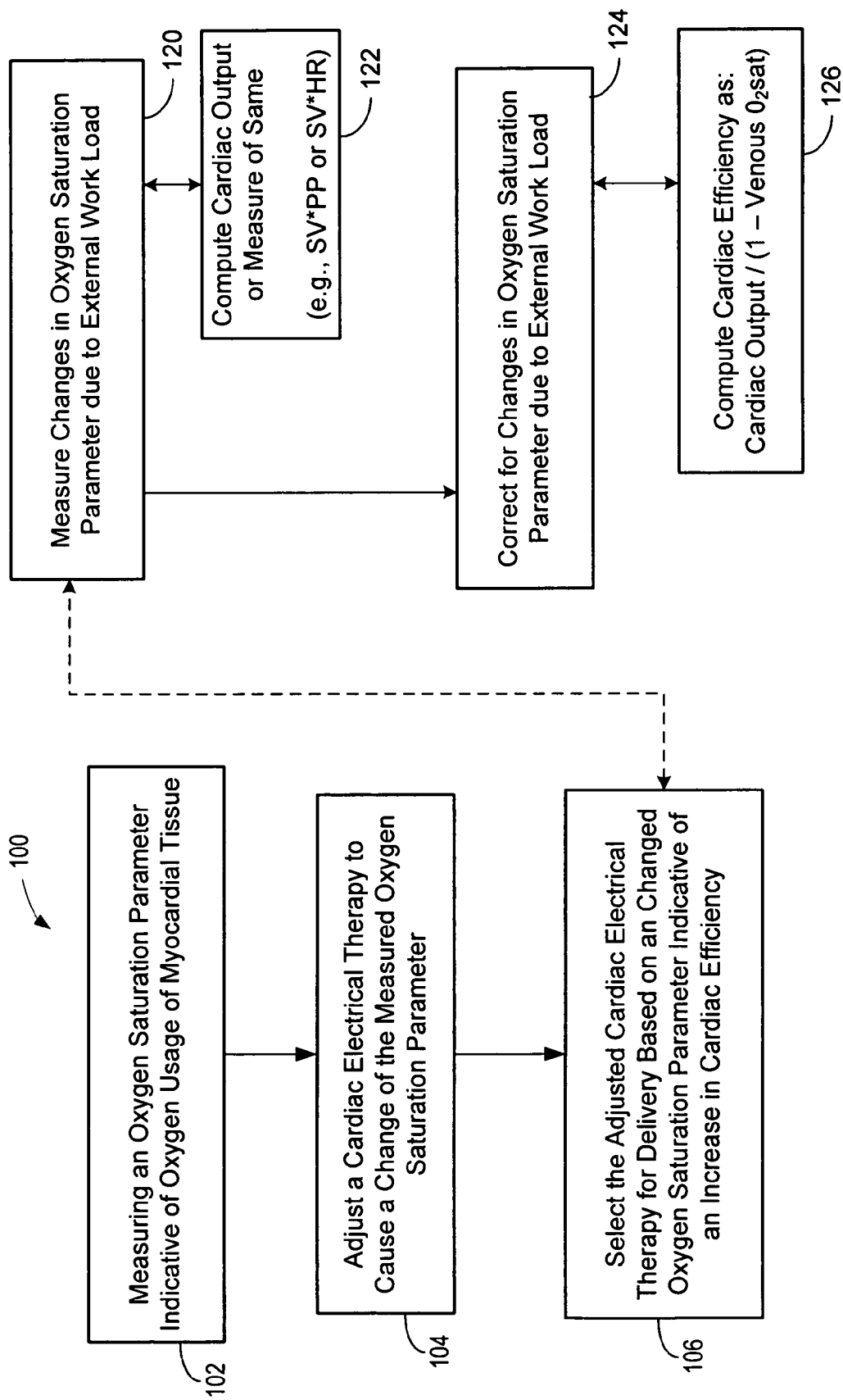

METHOD AND APPARATUS FOR IMPROVING CARDIAC EFFICIENCY BASED ON MYOCARDIAL OXYGEN CONSUMPTION

FIELD OF THE INVENTION

The present invention relates generally to a method and apparatus for cardiac pacing and, more particularly, to devices and methods for improving cardiac efficiency based on coronary venous oxygen saturation.

BACKGROUND OF THE INVENTION

Heart disease (cardiomyopathy) can cause a patient to exhibit symptoms of congestive heart failure (CHF). CHF is a result of the weakening of the heart's cardiac function characterized by reduced pumping capacity and efficiency. Chronic cardiac rhythm problems can also be the result of cardiomyopathy. The modification of the heart's structure that causes the reduction in pumping capacity also causes modification of the heart's electrical characteristics. The heart's electrical pathways can become stretched out of shape and chemically damaged. This makes arrhythmias much more likely to occur in CHF patients.

Implantation of a pacemaker is a preferred method of treatment for arrhythmias in CHF patients. Although many types of heart problems may require a pacemaker, one method of treatment suited for CHF patients is known as cardiac resynchronization therapy (CRT). CRT uses a pacemaker with multiple pacing leads to coordinate the heart's chambers to act together in a sequence that will pump blood more efficiently. It is likely that CRT candidates will have various forms of cardiomyopathy, and these patients may exhibit other measurable symptoms of reduced cardiac function besides arrhythmia.

SUMMARY OF THE INVENTION

The present invention is directed to improving cardiac efficiency and, more particularly, to devices and methods for improving cardiac efficiency based on myocardial oxygen consumption. According to embodiments of the present invention, methods of improving cardiac efficiency involve measuring, patient-internally, an oxygen saturation parameter indicative of oxygen usage of myocardial tissue of the heart. Methods of the present invention further involve adjusting a cardiac electrical therapy to cause a change of the measured oxygen saturation parameter, and selecting the adjusted cardiac electrical therapy for delivery based on a changed oxygen saturation parameter indicative of an increase in cardiac efficiency. Such methods may involve monitoring the oxygen saturation parameter to detect a change indicative of a change in the patient's cardiac efficiency.

According to one approach, measuring the oxygen saturation parameter involves measuring the oxygen saturation parameter in a coronary vein of the patient's heart. According to another approach, measuring the oxygen saturation parameter involves measuring the oxygen saturation parameter in the great cardiac vein of the patient's heart.

According to another approach, systems and methods may be directed to modifying regional cardiac efficiency. For example, a global oxygen saturation parameter indicative of oxygen usage of myocardial tissue of the entire left ventricle may be measured, patient-internally. A local oxygen saturation parameter indicative of oxygen usage in a region of the left ventricle may be measured, patient-internally. A cardiac electrical therapy may be adjusted based on the difference between the global and local oxygen saturation parameters, so as to improve regional cardiac efficiency. The global oxygen saturation parameter may be measured using a sensor located in the great cardiac vein, and the local oxygen saturation parameter may be measured using a sensor located in a cardiac vein draining the region of the left ventricle of interest.

Methods of the present invention may involve correcting for changes of the measured oxygen saturation parameter due to external work load. Correcting for changes of the measured oxygen saturation parameter due to external work load may involve computing a measure proportional to the patient's cardiac output based on the patient's heart rate and a measure of stroke volume.

According to one approach, selecting the adjusted cardiac electrical therapy involves computing the patient's cardiac efficiency based on a relationship defined by $$\frac{(SV \cdot PP)}{(1 - O_2)},$$

where SV is the associated stroke volume measurement, PP is the associated pulse pressure measurement, and $O_2$ is the oxygen saturation level measurement.

According to another approach, selecting the adjusted cardiac electrical therapy involves computing the patient's cardiac efficiency based on a relationship defined by $$\frac{(SV \cdot HR)}{(1 - O_2)},$$

where SV is the associated stroke volume measurement, HR is the associated heart rate, and $O_2$ is the oxygen saturation level measurement.

The cardiac electrical therapy that is adjusted to cause a change of the measured oxygen saturation parameter may be a pacing therapy. Adjustment of the cardiac electrical therapy may be effected by adjusting an atrioventricular (A-V) delay of the pacing therapy. Adjustment of the cardiac electrical therapy may be effected by adjusting a pacing rate of the pacing therapy. Adjustment of the cardiac electrical therapy may be effected by adjusting a pacing site for the pacing therapy.

The cardiac electrical therapy that is adjusted to cause a change of the measured oxygen saturation parameter may be a resynchronization therapy delivered to the heart. For example, the cardiac electrical therapy may be a bi-ventricular pacing therapy, and adjusting the cardiac electrical therapy may involve adjusting an inter-ventricular delay of the bi-ventricular pacing therapy.

In accordance with another embodiment, an apparatus for delivering a cardiac electrical therapy to a heart includes a lead having at least one electrode and configured to be positionable within vasculature of the heart. A blood oxygen saturation sensor is provided on the lead. The blood oxygen saturation sensor is configured to measure an oxygen saturation parameter indicative of oxygen usage of myocardial tissue of the heart.

The apparatus further includes an implantable housing, and a pulse generator disposed in the housing and coupled to the lead. A processor is disposed in the implantable housing and coupled to the pulse generator. The processor is configured to adjust a cardiac electrical therapy delivered to the heart to cause a change of the measured oxygen saturation parameter and select the adjusted cardiac electrical therapy for delivery based on a changed oxygen saturation parameter indicative of an increase in cardiac efficiency. The pulse generator is preferably configured to deliver a pacing therapy to the heart, such as a resynchronization therapy.

In one implementation, the blood oxygen saturation sensor is configured for placement within a coronary vein of the heart. In another implementation, the blood oxygen saturation sensor is configured for placement within the great cardiac vein of the heart.

The apparatus may include a sensor configured to sense one or more parameters indicative of stroke volume, and the processor may be configured to compute the patient's cardiac output using the one or more parameters indicative of stroke volume and a heart rate parameter developed by the pulse generator. The processor may be configured to correct for changes of the measured oxygen saturation parameter due to external work load using the patient's computed cardiac output. The sensor may be an intracardiac impedance sensor.

In accordance with a further embodiment, an apparatus for delivering a cardiac electrical therapy to a heart includes a lead system having at least one electrode and configured to be positionable within vasculature of the heart. The lead system includes a first blood oxygen sensor and a second blood oxygen sensor. The first blood oxygen saturation sensor is configured to measure a global oxygen parameter indicative of oxygen usage of myocardial tissue of the entire left ventricle. The second blood oxygen sensor is configured to measure a local oxygen saturation parameter indicative of oxygen usage of myocardial tissue of a region of the left ventricle. For example, the first blood oxygen sensor may be located in the great cardiac vein. The second blood oxygen sensor may be located in a cardiac vein draining the region of the left ventricle of interest.

The apparatus further includes an implantable housing, and a pulse generator disposed in the housing and coupled to the lead system. A processor is disposed in the implantable housing and coupled to the pulse generator. The processor is configured to adjust a cardiac electrical therapy delivered to the heart based on the difference between the global and local oxygen saturation parameters. The pulse generator is preferably configured to deliver a pacing therapy to the heart, such as a resynchronization therapy. The cardiac electrical therapy, according to this embodiment, is adjusted to modify or increase regional cardiac efficiency.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 1A illustrates various processes of a method of improving cardiac efficiency in accordance with an embodiment of the present invention;

FIG. 1B shows additional processes that may be implemented as part of the method of FIG. 1A;

Figure 1C:
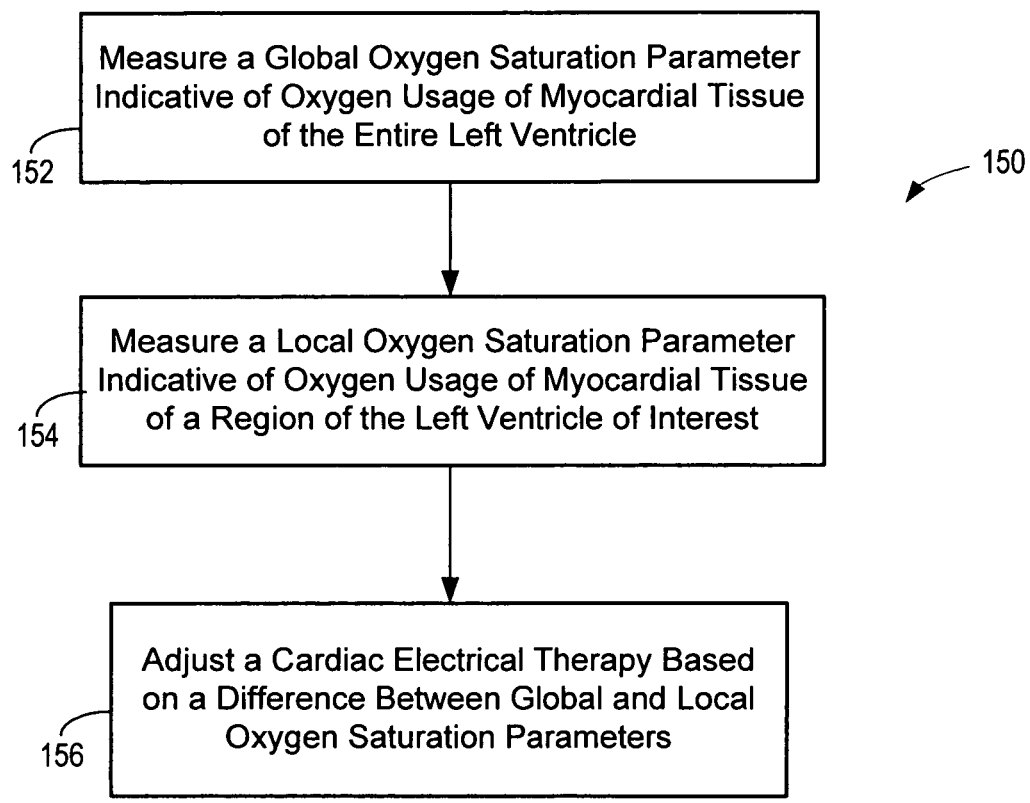
FIG. 1C illustrates various processes of a method of improving regional cardiac efficiency in accordance with an embodiment of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF THE VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

An implanted device in accordance with the present invention may include one or more of the features, structures, methods, or combinations thereof described hereinbelow. For example, a cardiac stimulator may be implemented to include one or more of the advantageous features and/or processes described below. It is intended that such a monitor, stimulator, or other implanted or partially implanted device need not include all of the features described herein, but may be implemented to include selected features that provide for useful structures and/or functionality. Such devices and/or methods may be implemented to provide a variety of therapeutic or diagnostic functionality.

A wide variety of implantable cardiac stimulation devices may be configured to implement cardiac efficiency enhancement methodologies of the present invention. A non-limiting, representative list of such devices includes pacemakers, cardiovertors, defibrillators, resynchronizers, and other cardiac therapy delivery devices. These devices may be configured with a variety of electrode arrangements, including transvenous, endocardial, and epicardial electrodes (i.e., intrathoracic electrodes), and may also include subcutaneous, non-intrathoracic electrodes, including can, header, and indifferent electrodes, and subcutaneous array or lead electrodes (i.e., non-intrathoracic electrodes).

Devices implemented in accordance with the present invention are generally referred to herein as a patient implantable medical device (PIMD). A PIMD implemented in accordance with the present invention may incorporate one or more of the electrode types identified above and/or combinations thereof.

Devices and method of the present invention provide for improved cardiac efficiency based on coronary venous oxygen saturation. Devices and methods of the present invention may be implemented to control therapy applied to a heart by minimizing myocardial oxygen consumption for a given external workload, so as to increase, maximize or optimize cardiac efficiency. Myocardial oxygen consumption is assessed by measuring oxygen saturation in a coronary vein or the great cardiac vein, where a decrease in oxygen saturation corresponds to an increase in myocardial oxygen consumption. Global and local myocardial oxygen consumption of the left ventricle, for example, may be assessed by measuring oxygen saturation in the great cardiac vein and a cardiac vein draining the left ventricular region of interest. Heart rate or other measures of external workload may be monitored to insure that oxygen consumption changes are not due to changes in workload.

Devices in accordance with the present invention include an oxygen saturation sensor configured to measure the oxygen saturation of blood. When an oxygen saturation sensor in accordance with the present invention is positioned within the cardiac venous system, myocardial oxygen consumption, including global and local myocardial oxygen consumption, may be determined, and oxygen consumption information may be used to improve global and/or regional cardiac efficiency.

Cardiac efficiency can be useful measure of heart performance. Measurements of cardiac efficiency can be beneficially applied to adaptively change therapy parameters, for example, of a cardiac pacing device, cardiac defibrillation device, or cardiac resynchronizing device. Further, analyzing cardiac efficiency can provide a pacing system with the ability to measure and adapt to heart activity over a long period of time in order to measure and improve the efficacy of the pacing treatment for a patient.

Embodiments of the present invention involve use of a lead-based oxygen saturation sensor for monitoring myocardial oxygen consumption. In some configurations, an oxygen saturation sensor may be configured for positioning in the great cardiac vein. In this configuration, the oxygen saturation sensor monitors the oxygen content of blood returning from the myocardial capillary bed and is thus sensitive to changes in myocardial workload. Any increase in myocardial oxygen consumption is reflected as a decrease in oxygen saturation in the great cardiac vein.

In other configurations, an oxygen saturation sensor may be configured for positioning in a coronary vein. In this configuration, the oxygen saturation sensor monitors oxygen consumption of blood from the region draining into the particular coronary vein. In further configurations, a first oxygen saturation sensor may be configured for positioning in the great cardiac vein, and a second oxygen saturation sensor may be configured for positioning in a cardiac vein draining a cardiac region of interest, thus yielding global and regional oxygen saturation measurements. Cardiac electrical therapies may be applied and adjusted in accordance with the present invention to increase the oxygen saturation of returning blood based on global and/or local oxygen saturation measurements.

According to various embodiments, systems and methods of the present invention are directed to cardiac electrical therapies applied to improve synchronization between dyssynchronously contracting heart chambers or portions thereof. Because different regions of the heart contract and relax dyssynchronously, some of the work involved in myocyte shortening is wasted on stretching other relaxed myocytes leading to an inefficient contraction and increased myocardial oxygen consumption reflected in a relatively low oxygen saturation in the great cardiac vein, for example. Resynchronization of the heart may be effected to increase the oxygen saturation level and the therapy may be titrated until the oxygen saturation level is increased, maximized or otherwise optimized. Therapy titration may involve adjustment of a pacing site, pacing vector, A-V delay, interventricular (V-V) delay, or other pacing/resynchronization parameter.

Changes in external work load, due to exercise for example, can change the oxygen saturation level. An independent measure of cardiac output may be monitored to correct for this effect. Output of the heart is termed cardiac output, and is measured in terms of liters per minute. Cardiac output may be defined as the product of heart rate and stroke volume. By monitoring heart rate and measuring stroke volume, such as by use of intracardiac impedance measurements, it is possible to compute cardiac output or a measure proportional to cardiac output. Cardiac efficiency may then be computed based on the computed cardiac output and a measure of venous oxygen saturation. Devices of the present invention may be configured to increase, maximize or optimize the value of cardiac efficiency, on a continuous or scheduled basis.

Turning now to FIG. 1A, there is illustrated various processes of a method of improving cardiac efficiency in accordance with an embodiment of the present invention. The method 100 illustrated in FIG. 1A involves measuring 102 an oxygen saturation parameter indicative of oxygen usage of myocardial tissue. A cardiac electrical therapy is adjusted 104 to cause a change of the measured oxygen saturation parameter. The adjusted cardiac electrical therapy is selected 106 for delivery based on a changed oxygen saturation parameter indicative of an increase in cardiac efficiency.

FIG. 1B shows additional processes that may be implemented as part of the method of FIG. 1A. As was discussed previously, changes in external work load can change the oxygen saturation level. An independent measure of cardiac output may be measured 120 and monitored to correct for this effect. One approach illustrated in FIG. 1B involves computing 122 cardiac output or a measure of cardiac output. According to one approach, cardiac output may be computed as SV·PP, where SV is a measure of stroke volume and PP is a measure of pulse pressure. According to another approach, cardiac output may be computed as SV·HR, where SV is a measure of stroke volume and HR is a measure of heart rate.

The method of FIG. 1B further involves correcting 124 for changes in the oxygen saturation parameter due to external workload. Such corrections may be based on changes in cardiac efficiency, which may be computed 126 as:

$$\frac{(Cardiac\_Output)}{(1 - Venous\_O_2\_Saturation)}.$$

FIG. 1C illustrates various processes of a method of improving regional cardiac efficiency in accordance with an embodiment of the present invention. The method 150 illustrated in FIG. 1C involves measuring 152 a global oxygen saturation parameter indicative of oxygen usage of myocardial tissue of the entire left ventricle. A local oxygen saturation parameter indicative of oxygen usage in a region of the left ventricle of interest is measured 154. A cardiac electrical therapy is adjusted 156 based on the difference between the global and local oxygen saturation parameters, so as to improve regional cardiac efficiency. The global oxygen saturation parameter may be measured in the great cardiac vein, and the local oxygen saturation parameter may be measured in a cardiac vein draining the region of the left ventricle of interest.

Figure 2:
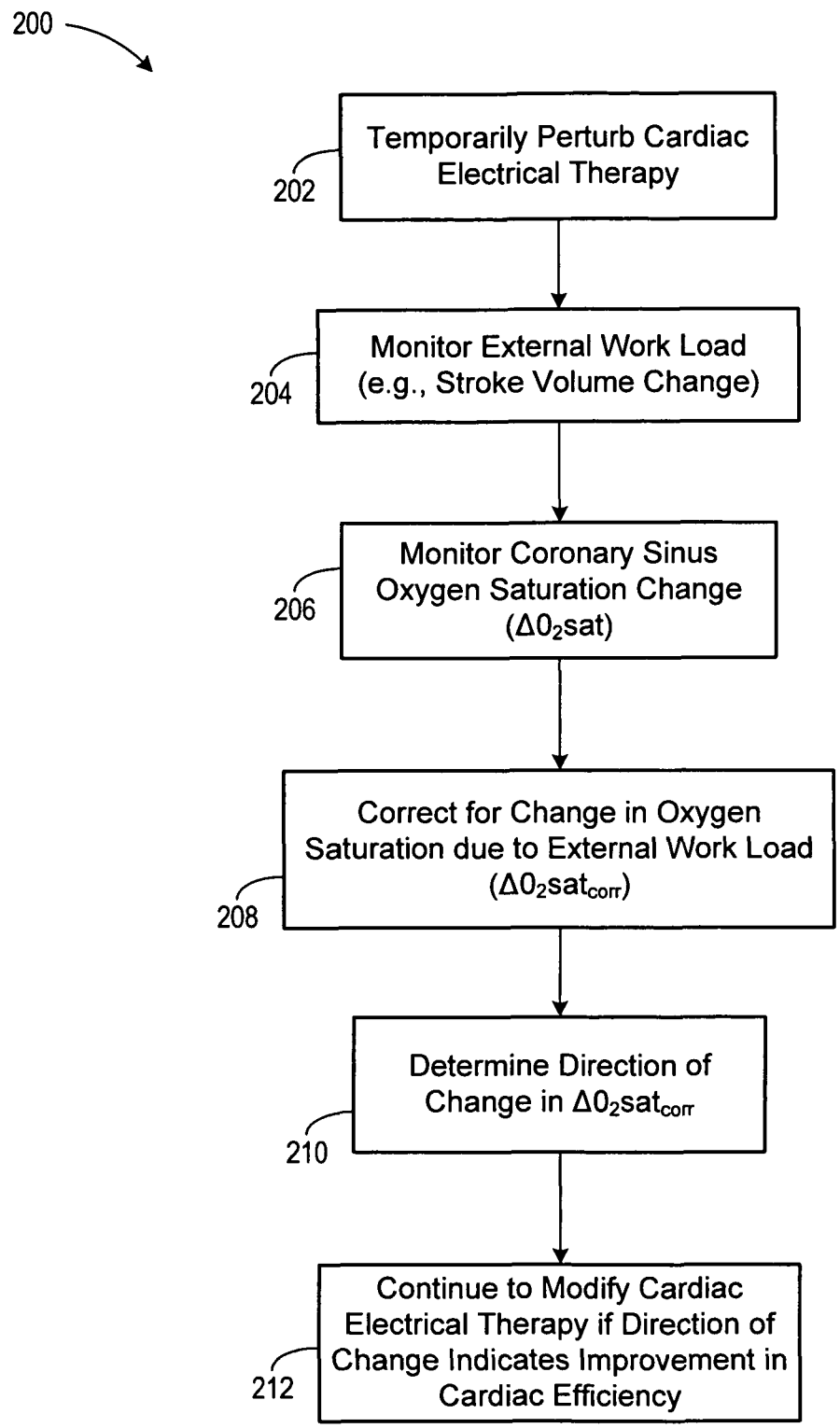
FIG. 2 illustrates a method of modifying a cardiac electrical therapy to improve cardiac efficiency in accordance with an embodiment of the present invention.

FIG. 2 illustrates a method 200 of modifying a cardiac electrical therapy to improve cardiac efficiency in accordance with an embodiment of the present invention. Method 200 involves temporarily perturbing 202 cardiac electrical therapy delivered to a patient. During a time in which the cardiac electrical therapy is perturbed, external work load is monitored 204, such as by monitoring changes in stroke volume. Coronary sinus oxygen saturation changes are also monitored 206 during this time. Any change in oxygen saturation due to external work load is corrected 208. The direction of oxygen saturation change is determined 210. The cardiac electrical therapy is further modified 212 if the direction of oxygen saturation change indicates improvement in cardiac efficiency.

Figure 3:
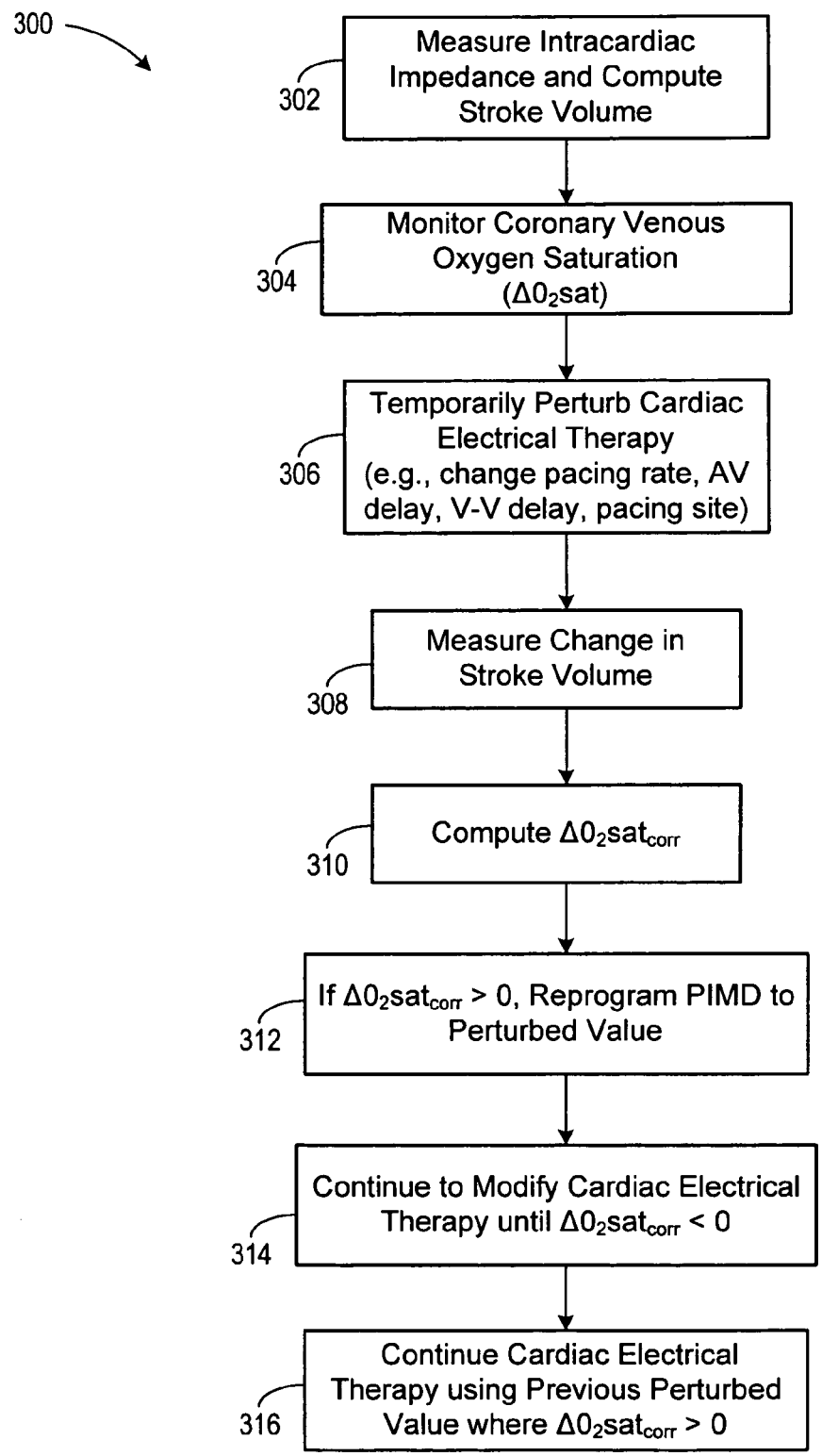
FIG. 3 illustrates another method of modifying a cardiac electrical therapy to improve cardiac efficiency in accordance with an embodiment of the present invention.

FIG. 3 illustrates another method 300 of modifying a cardiac electrical therapy to improve cardiac efficiency in accordance with an embodiment of the present invention. Method 300 involves measuring intracardiac impedance and computing stroke volume 302 using the intracardiac impedance measurement. Coronary venous oxygen saturation is monitored 304. Cardiac electrical therapy delivered to the patient is temporarily perturbed 306, such as by changing the pacing rate, A-V delay, V-V delay, pacing site or other therapy parameter.

Changes in stroke volume during a time in which the cardiac electrical therapy is perturbed are measured 308. Oxygen saturation is computed 310 and corrections are made to the computed oxygen saturation due to external work load. If a change in the corrected oxygen saturation value resulting from the perturbed therapy is positive (i.e., $\Delta O_2 sat_{corr} > 0$), then the PIMD is reprogrammed 312 to deliver therapy based on the changed parameter of the perturbed therapy. A positive change in the corrected oxygen saturation value represents a decrease in myocardial oxygen consumption and increase in cardiac efficiency.

The cardiac electrical therapy may be further modified 314 until the corrected oxygen saturation value resulting from the modified perturbed therapy is negative (i.e., $\Delta O_2 sat_{corr} < 0$). The PIMD is reprogrammed 316 to deliver therapy based on the previous changed parameter of the perturbed therapy (i.e., previous non-negative value of $\Delta O_2 sat_{corr}$). In this manner, cardiac electrical therapy (e.g., resynchronization therapy) may be titrated until the oxygen saturation level is maximized.

Figure 4:
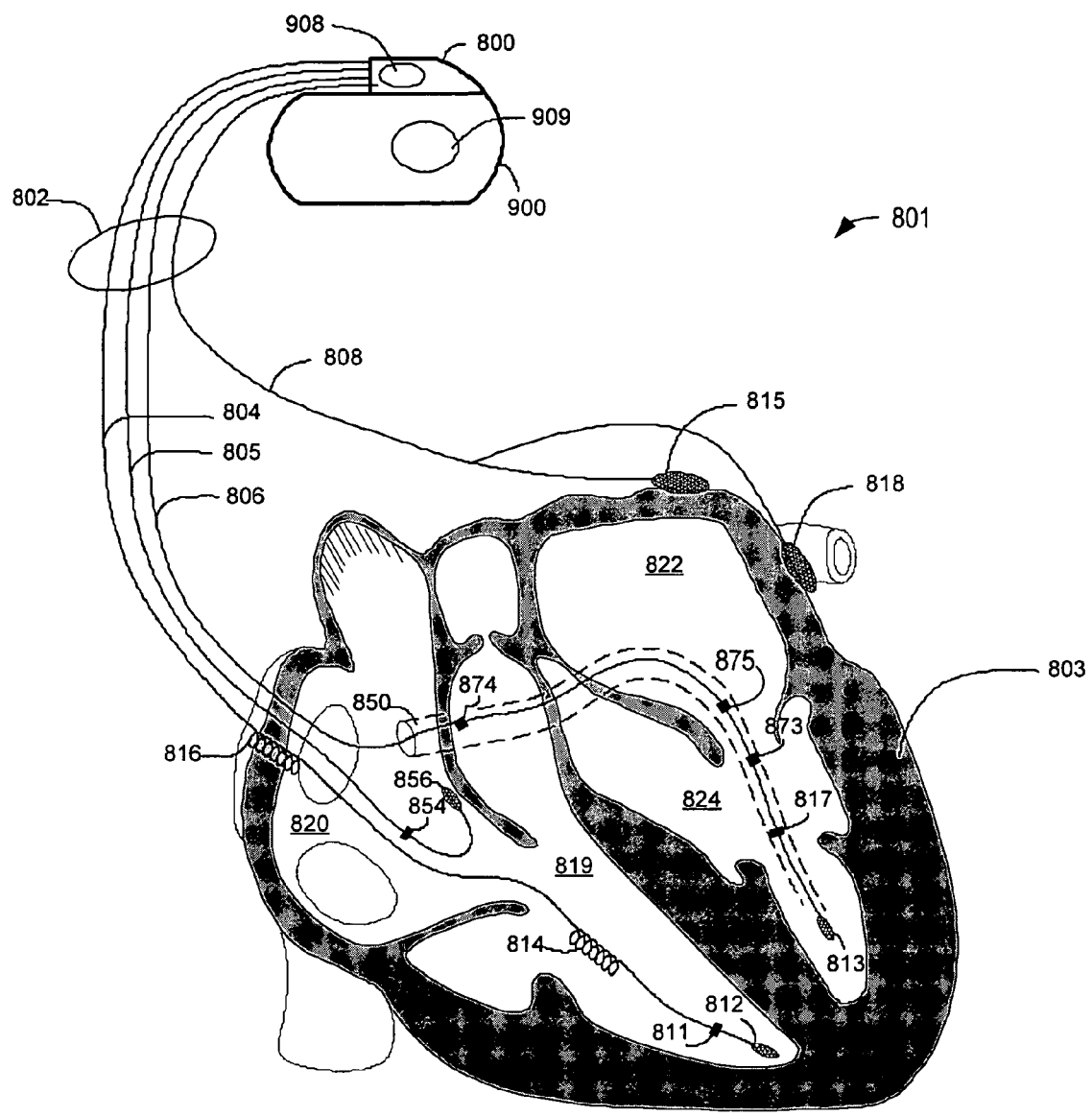
FIG. 4 shows a system configured to deliver and titrate cardiac electrical therapy to improve cardiac efficiency in accordance with an embodiment of the present invention.

Turning now to FIG. 4, a system in accordance with the present invention is shown having a lead system deployed within a heart. System 801 includes a PIMD 800 with a lead system 802 that is designed for implantation to facilitate cardiac resynchronization therapy. The lead system 802 is coupled to a detection/energy delivery system 900, which detects cardiac activity and delivers appropriate therapy via the lead system 802.

The detector/energy delivery system 900 typically includes a power supply and programmable circuit (e.g., microprocessor) coupled to an analog to digital (A-D) converter. Various lead system devices, such as electrodes, pressure sensors, and oxygen saturation sensors can interface to the A-D converter for sensing/data collection. Alternatively, analog conditioning (e.g., filtering) may be applied to sensor signals before interfacing with the A-D converter. The detector/energy delivery system 900 also utilizes an energy delivery system. The energy delivery system may include charge capacitors and signal conditioning circuitry known in the art. The energy delivery system may interface to the programmable circuit through a D-A converter. Components and functionality of the detector/energy delivery system 900 will be further described below with reference to FIG. 5.

Referring still to FIG. 4 of the drawings, the PIMD system 801 may be used to implement methods for improving cardiac efficiency based on venous oxygen saturation in accordance with the present invention. The PIMD system 801 in FIG. 4 is illustrated having the PIMD 800 electrically and physically coupled to the lead system 802. The housing and/or header of the PIMD 800 may incorporate one or more electrodes 908, 909 used to provide electrical stimulation energy to the heart and to sense cardiac electrical activity. The PIMD 800 may utilize all or a portion of the PIMD housing as a can electrode 909. The PIMD 800 may include an indifferent electrode positioned, for example, on the header or the housing of the PIMD 800. If the PIMD 800 includes both a can electrode 909 and an indifferent electrode 908, the electrodes 908, 909 typically are electrically isolated from each other.

The lead system 802 is used to provide pacing signals to the heart 803, detect electric cardiac signals produced by the heart 803, and deliver electrical energy to the heart 803 under certain predetermined conditions, such as to improve cardiac output and/or to treat cardiac arrhythmias. The lead system 802 may include one or more electrodes used for pacing, sensing, and/or defibrillation. In the embodiment shown in FIG. 4, the lead system 802 includes an intracardiac right ventricular (RV) lead system 804, an intracardiac right atrial (RA) lead system 805, an intracardiac left ventricular (LV) lead system 806, and an extracardiac left atrial (LA) lead system 808. The lead system 802 of FIG. 4 illustrates one of many possible PIMD configurations. It is understood that more or fewer leads and/or electrodes of varying type may be used.

The right ventricular lead system 804 illustrated in FIG. 4 includes an SVC-coil 816, an RV-coil 814, an RV-ring electrode 811, and an RV-tip electrode 812. The right ventricular lead system 804 extends through the right atrium 820 and into the right ventricle 819. In particular, the RV-tip electrode 812, RV-ring electrode 811, and RV-coil electrode 814 are positioned at appropriate locations within the right ventricle 819 for sensing and delivering electrical stimulation pulses to the heart. The SVC-coil 816 is positioned at an appropriate location within the right atrium chamber 820 of the heart 803 or a major vein leading to the right atrial chamber 820 of the heart 803.

In one configuration, the RV-tip electrode 812 referenced to the can electrode 909 may be used to implement unipolar pacing and/or sensing in the right ventricle 819. Bipolar pacing and/or sensing in the right ventricle may be implemented using the RV-tip 812 and RV-ring 811 electrodes. In yet another configuration, the RV-ring 811 electrode may optionally be omitted, and bipolar pacing and/or sensing may be accomplished using the RV-tip electrode 812 and the RV-coil 814, for example. The right ventricular lead system 804 may be configured as an integrated bipolar pace/shock lead. The RV-coil 814 and the SVC-coil 816 are defibrillation electrodes.

The left ventricular lead 806 includes an LV distal electrode 813 and an LV proximal electrode 817 located at appropriate locations on the surface of, or about, the left ventricle 824 for pacing and/or sensing the left ventricle 824. The left ventricular lead 806 may be guided into the right atrium 820 of the heart via the superior vena cava. From the right atrium 820, the left ventricular lead 806 may be deployed into the coronary sinus ostium, the opening of the coronary sinus 850. The lead 806 may be guided through the coronary sinus 850 to a coronary vein of the left ventricle 824. This vein is used as an access pathway for leads to reach the surfaces of the left ventricle 824 which are not directly accessible from the right side of the heart. Lead placement for the left ventricular lead 806 may be achieved via subclavian vein access and a pre-formed guiding catheter for insertion of the LV electrodes 813, 817 adjacent to the left ventricle.

Unipolar pacing and/or sensing in the left ventricle may be implemented, for example, using the LV distal electrode referenced to the can electrode 909. The LV distal electrode 813 and the LV proximal electrode 817 may be used together as bipolar sense and/or pace electrodes for the left ventricle. The left ventricular lead 806 and the right ventricular lead 804, in conjunction with the PIMD 800, may be used to provide cardiac resynchronization therapy such that the ventricles of the heart are paced substantially simultaneously, or in phased sequence, to provide enhanced cardiac pumping efficiency in accordance with the present invention for patients suffering from congestive heart failure.

The right atrial lead 805 includes a RA-tip electrode 856 and an RA-ring electrode 854 positioned at appropriate locations in the right atrium 820 for sensing and pacing the right atrium 820. In one configuration, the RA-tip 856 referenced to the can electrode 909, for example, may be used to provide unipolar pacing and/or sensing in the right atrium 820. In another configuration, the RA-tip electrode 856 and the RA-ring electrode 854 may be used to provide bipolar pacing and/or sensing. The lead system 802 may include one or more extracardiac leads 808 having electrodes, e.g., epicardial electrodes or sensors 815, 818, positioned at locations outside the heart for sensing and/or pacing one or more heart chambers.

A system in accordance with the present invention may use a pressure reading obtained from a coronary vein in the left ventricle to provide an estimate of left ventricular pressure (LVP). The LVP is generally much more indicative of cardiac function than right ventricular pressure. The left ventricular end diastolic pressure (LVEDP), also referred to as pulse pressure (PP), is a measure that may be used to evaluate hemodynamic state. LVEDP can be measured from a coronary vein, for example, without exposing the patient to the risks involved in obtaining direct readings from the left ventricle or left atrium. Useful pressure sensors and sensing techniques are described in commonly owned U.S. Pat. Nos. 6,666,826 and 6,280,389, which are hereby incorporated herein by reference. It is understood that other sensors and techniques may be used to obtain a useful pressure measurement in the context of the present invention.

The left ventricular lead 806, as shown in FIG. 4, includes a pressure transducer 875. It is understood that the pressure transducer 875 may be integral to the left ventricular lead 806 or be disposed on a separate sensor lead or catheter. The pressure transducer 875 may take a variety of forms.

A suitable pressure transducer 875 is one formed as a micro-electrical-mechanical system (MEMS), for example. MEMS technology uses semiconductor techniques to build microscopic mechanical devices in silicon or similar materials. The pressure transducer 875 can include a micromachined capacitive or piezoresistive transducer exposed to the bloodstream. Other pressure transducer technologies, such as resistive strain gages, are known in the art and can also be employed as a pressure transducer 875. The pressure transducer 875 may be coupled to one or more conductors disposed along the length of the left ventricular lead 806. In the configuration shown in FIG. 4, the pressure transducer 875 is integrated with the left ventricular lead 806.

The left ventricular lead 806, as shown in FIG. 4, includes a blood oxygen sensor 873 or 874 used to determine blood oxygen saturation levels of blood from the myocardium. In one configuration, the left ventricular lead 806 or separate lead/catheter may include a blood oxygen sensor 874 implanted in the coronary sinus. In another configuration, the left ventricular lead 806 or separate lead/catheter may include a blood oxygen sensor 873 implanted in the great coronary vein.

Figure 5:
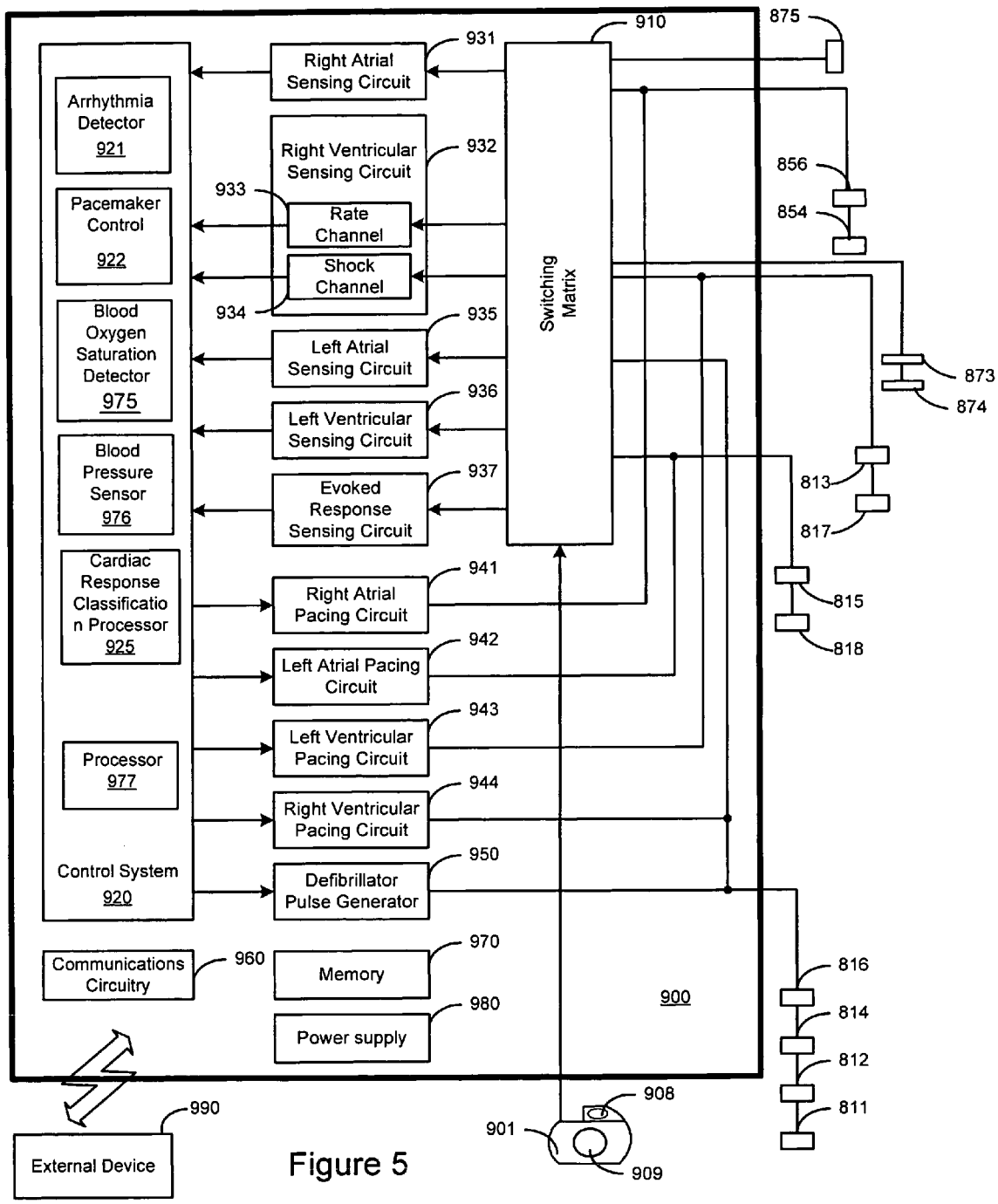
FIG. 5 shows an embodiment of a system suitable for implementing cardiac efficiency improvement methodologies of the present invention.

The blood oxygen sensor 873, 874 may take a variety of forms. A suitable blood oxygen sensor 873, 874 is one formed as a micro-electrical-mechanical system, for example. Useful MEMS blood oxygen saturation sensors are described in U.S. Pat. No. 5,776,060, which is hereby incorporated herein by reference. The blood oxygen sensor 873, 874 may also be implemented using a sensor configured for optical signal sensing, such as an optical blood oxygen saturation sensor or a pulse oximeter. A suitable pulse oximeter may include two light-emitting diodes and one photodetector, for example. Useful optical blood oxygen sensing systems and methods are described in commonly owned U.S. Patent Pub. No. 2004/0220629, which is hereby incorporated herein by reference Referring now to FIG. 5, there is shown an embodiment of a PIMD 900 suitable for implementing cardiac efficiency improvement methodologies of the present invention. FIG. 5 shows the PIMD 900 divided into functional blocks. It is understood by those skilled in the art that there exist many possible configurations in which these functional blocks can be arranged. The example depicted in FIG. 5 is one possible functional arrangement. Other arrangements are also possible. For example, more, fewer or different functional blocks may be used to describe a PIMD suitable for implementing cardiac efficiency improvement methodologies of the present invention. In addition, although the PIMD 900 depicted in FIG. 5 contemplates the use of a programmable microprocessor-based logic circuit, other circuit implementations may be utilized. It is also understood that the components and functionality depicted in FIG. 5 and elsewhere may be implemented in hardware, software, or a combination of hardware and software.

The PIMD 900 depicted in FIG. 5 includes circuitry for receiving cardiac signals from a heart and delivering electrical stimulation energy to the heart in the form of pacing pulses and/or defibrillation shocks. In one embodiment, the circuitry of the PIMD 900 is encased and hermetically sealed in a housing 901 suitable for implanting in a human body. Power to the PIMD 900 is supplied by an electrochemical battery 980. A connector block (not shown) is attached to the housing 901 of the PIMD 900 to allow for the physical and electrical attachment of the lead system conductors to the circuitry of the PIMD 900.

The PIMD 900 may be a programmable microprocessor-based system, including a control system 920 and a memory 970. The memory 970 may store parameters for various pacing, resynchronization, defibrillation, and sensing modes, along with other parameters. Further, the memory 970 may store data indicative of signals received by other components of the PIMD 900. The memory 970 may be used, for example, for storing historical information, impedance information, blood oxygen saturation information, blood pressure and flow information, perfusion information, heart sounds, heart movement, EGM information, therapy data, and/or other information, assuming appropriate sensors are provided. The historical data storage may include, for example, data obtained from long-term patient monitoring used for assessing cardiac efficiency, trending patient well-being, heart failure decompensation, or other diagnostic purposes. Historical data, as well as other information, may be transmitted to an external device 990 as needed or desired. In one embodiment, the external device 990 may include a communications interface of a networked patient management system, as is discussed below.

The control system 920 and memory 970 may cooperate with other components of the PIMD 900 to control the operations of the PIMD 900. The control system depicted in FIG. 5 incorporates a processor 925 for classifying cardiac responses to pacing stimulation. The control system 920 may include additional functional components including an arrhythmia detector 921, a pacemaker control circuit 922, and a template processor 923 for cardiac signal morphology analysis, along with other components for controlling the operations of the PIMD 900. The PIMD 900 may also include a processor 977 configured to perform cardiac output and efficiency computations. The processor 977 may be configured to cooperate with the pacemaker control circuit 922 to titrate therapy in accordance with the present invention.

Communications circuitry 960 may be implemented to provide communications between the PIMD 900 and an external programmer unit 990 and/or a networked patient management system. In one embodiment, the communications circuitry 960 and a programmer unit 990 communicate using a wire loop antenna and a radio frequency telemetric link, as is known in the art, to receive and transmit signals and data between the programmer unit 990 and the communications circuitry 960. In this manner, programming commands and other information may be transferred to the control system 920 of the PIMD 900 from the programmer unit 990 during and after implant.

The communications circuitry 960 may also allow the PIMD to communicate with one or more receiving devices or systems situated external to the PIMD 900. By way of example, the PIMD may communicate with a patient-worn, portable or bedside communication system via the communications circuitry 960. In one configuration, one or more physiologic or non-physiologic sensors (subcutaneous, cutaneous, or external of patient) of a PIMD system may be equipped with a short-range wireless communication interface, such as an interface conforming to a known communications standard, such as Bluetooth or IEEE 802 standards. Data acquired by such sensors may be communicated to the PIMD 900 via the communications circuitry 960. It is noted that physiologic or non-physiologic sensors equipped with wireless transmitters or transceivers may communicate with a receiving system external of the patient. The external sensors in communication with the PIMD 900 may be used to facilitate patient well-being assessment, heart failure decompensation trending/tracking, cardiac resynchronization therapy adjustment and optimization, and other purposes.

In the embodiment of the PIMD 900 illustrated in FIG. 5, electrodes RA-tip 856, RA-ring 854, RV-tip 812, RV-ring 811, RV-coil 814, SVC-coil 816, LV distal electrode 813, LV proximal electrode 817, LA distal electrode 818, LA proximal electrode 815, indifferent electrode 908, and can electrode 909 are coupled through a switch matrix 910 to sensing circuits 931-937.

A right atrial sensing circuit 931 serves to detect and amplify electrical signals from the right atrium of the heart. Bipolar sensing in the right atrium may be implemented, for example, by sensing voltages developed between the RA-tip 856 and the RA-ring 854. Unipolar sensing may be implemented, for example, by sensing voltages developed between the RA-tip 856 and the can electrode 909. Outputs from the right atrial sensing circuit are coupled to the control system 920.

A right ventricular sensing circuit 932 serves to detect and amplify electrical signals from the right ventricle of the heart. The right ventricular sensing circuit 932 may include, for example, a right ventricular rate channel 933 and a right ventricular shock channel 934. Right ventricular cardiac signals sensed through use of the RV-tip 812 electrode are right ventricular near-field signals and are denoted RV rate channel signals. A bipolar RV rate channel signal may be sensed as a voltage developed between the RV-tip 812 and the RV-ring 811. Alternatively, bipolar sensing in the right ventricle may be implemented using the RV-tip electrode 812 and the RV-coil 814. Unipolar rate channel sensing in the right ventricle may be implemented, for example, by sensing voltages developed between the RV-tip 812 and the can electrode 909.

Right ventricular cardiac signals sensed through use of the RV-coil electrode 814 are far-field signals, also referred to as RV morphology or RV shock channel signals. More particularly, a right ventricular shock channel signal may be detected as a voltage developed between the RV-coil 814 and the SVC-coil 816. A right ventricular shock channel signal may also be detected as a voltage developed between the RV-coil 814 and the can electrode 909. In another configuration, the can electrode 909 and the SVC-coil electrode 816 may be electrically shorted and a RV shock channel signal may be detected as the voltage developed between the RV-coil 814 and the can electrode 909/SVC-coil 816 combination.

Left atrial cardiac signals may be sensed through the use of one or more left atrial electrodes 815, 818, which may be configured as epicardial electrodes. A left atrial sensing circuit 935 serves to detect and amplify electrical signals from the left atrium of the heart. Bipolar sensing and/or pacing in the left atrium may be implemented, for example, using the LA distal electrode 818 and the LA proximal electrode 815. Unipolar sensing and/or pacing of the left atrium may be accomplished, for example, using the LA distal electrode 818 to can vector 909 or the LA proximal electrode 815 to can vector 909.

Referring still to FIG. 5, a left ventricular sensing circuit 936 serves to detect and amplify electrical signals from the left ventricle of the heart. Bipolar sensing in the left ventricle may be implemented, for example, by sensing voltages developed between the LV distal electrode 813 and the LV proximal electrode 817. Unipolar sensing may be implemented, for example, by sensing voltages developed between the LV distal electrode 813 or the LV proximal electrode 817 and the can electrode 909.

Optionally, an LV coil electrode (not shown) may be inserted into the patient's cardiac vasculature, e.g., the coronary sinus, adjacent the left heart. Signals detected using combinations of the LV electrodes, 813, 817, LV coil electrode (not shown), and/or can electrodes 909 may be sensed and amplified by the left ventricular sensing circuitry 936. The output of the left ventricular sensing circuit 936 is coupled to the control system 920.

Blood oxygen saturation signals may be sensed through the use of one or more blood oxygen sensor(s) 873, 874, as described above with reference to FIG. 4. The control system 920 includes a blood oxygen saturation detector 975 that serves to measure the blood oxygen saturation using the sensed signal from the blood oxygen sensor(s) 873, 874. The blood oxygen saturation level detected from the venous system of the heart may be used to improve cardiac efficiency in accordance with the present invention.

A PIMD of the present invention may be used within the structure of an advanced patient management (APM) medical system. Advanced patient management systems may allow physicians to remotely and automatically monitor cardiac and respiratory functions, as well as other patient conditions. In one example, implantable cardiac rhythm management systems, such as cardiac pacemakers, defibrillators, and resynchronization devices, may be equipped with various telecommunications and information technologies that enable real-time data collection, diagnosis, and treatment of the patient. Various embodiments described herein may be used in connection with advanced patient management. Methods, structures, and/or techniques described herein, which may be adapted to provide for remote patient/device monitoring, trending, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

Various embodiments described herein may be used in connection with congestive heart failure (CHF) monitoring, trending, diagnosis, and/or therapy and therapy titration. A PIMD of the present invention may incorporate CHF features involving dual-chamber or bi-ventricular pacing/therapy, cardiac resynchronization therapy, cardiac function optimization, or other CHF related methodologies. For example, a PIMD of the present invention may incorporate features of one or more of the following references: commonly owned U.S. patent application Ser. No. 10/270,035, filed Oct. 11, 2002, entitled "Timing Cycles for Synchronized Multisite Cardiac Pacing;" and U.S. Pat. Nos. 6,411,848; 6,285,907; 4,928,688; 6,459,929; 5,334,222; 6,026,320; 6,371,922; 6,597,951; 6,424,865; and 6,542,775, each of which is hereby incorporated herein by reference.

A PIMD may be used to implement various diagnostic functions, which may involve performing rate-based, pattern and rate-based, and/or morphological tachyarrhythmia discrimination analyses. Subcutaneous, cutaneous, and/or external sensors may be employed to acquire physiologic and non-physiologic information for purposes of enhancing tachyarrhythmia detection and termination. It is understood that configurations, features, and combination of features described in the present disclosure may be implemented in a wide range of implantable medical devices, and that such embodiments and features are not limited to the particular devices described herein.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of improving cardiac efficiency, comprising:
measuring, patient-internally in at least one of a coronary vein and the great cardiac vein of the patient's heart, oxygen saturation indicative of oxygen usage of myocardial tissue of the heart;
measuring cardiac stroke volume;
calculating a cardiac efficiency parameter based on the measured oxygen saturation and the measured stroke volume;
adjusting a cardiac electrical therapy to cause a change of the measured oxygen saturation;
calculating a change in the cardiac efficiency parameter resulting from the cardiac electrical therapy adjustment;
determining whether the adjustment in the cardiac electrical therapy decreased or increased cardiac efficiency based on the calculated change in the cardiac efficiency parameter; and
selecting the adjusted cardiac electrical therapy for delivery if the adjustment of the cardiac electrical therapy was determined to increase cardiac efficiency, wherein at least some of the steps of calculating the cardiac efficiency parameter, calculating the change, determining, and selecting are performed at least in part by circuitry.

2. The method of claim 1, wherein measuring the oxygen saturation comprises measuring the oxygen saturation in the coronary vein of the patient's heart.

3. The method of claim 1, wherein measuring the oxygen saturation comprises measuring the oxygen saturation in the great cardiac vein of the patient's heart.

4. The method of claim 1, wherein calculating the change in cardiac efficiency parameter comprises correcting for changes of the measured oxygen saturation due to external work load using the measured stroke volume.

5. The method of claim 1, wherein determining whether the adjustment of the cardiac electrical therapy decreased or increased cardiac efficiency comprises determining whether oxygen saturation increased or decreased based on the adjustment of the cardiac electrical therapy, the therapy adjustment being determined to increase cardiac efficiency if higher oxygen saturation is measured after the therapy adjustment and the therapy adjustment being determined to decrease cardiac efficiency if lower oxygen saturation is measured after the therapy adjustment.

6. The method of claim 1, wherein calculating the change in cardiac efficiency parameter comprises computing the patient's cardiac efficiency based on a relationship defined by $$\frac{(SV \cdot PP)}{(1-O_2)},$$

where SV is the associated stroke volume measurement, PP is the associated pulse pressure measurement, and O2 is the oxygen saturation level measurement.

7. The method of claim 1, wherein calculating the change in cardiac efficiency parameter comprises computing the patient's cardiac efficiency based on a relationship defined by where $$\frac{(SV \cdot HR)}{(1-O_2)},$$

SV is the associated stroke volume measurement, HR is the associated heart rate, and O2 is the oxygen saturation level measurement.

8. The method of claim 1, wherein calculating the cardiac efficiency parameter comprises calculating a first cardiac efficiency by dividing stroke volume by oxygen saturation using stroke volume and oxygen saturation measurements taken before the cardiac electrical therapy adjustment, and wherein calculating the change in cardiac efficiency parameter comprises calculating a second cardiac efficiency by dividing stroke volume by oxygen saturation using stroke volume and oxygen saturation measurements taken after the cardiac electrical therapy adjustment and determining the difference between the first and second cardiac efficiency calculations.

9. The method of claim 1, wherein the cardiac electrical therapy comprises a pacing therapy.

10. The method of claim 1, wherein the cardiac electrical therapy comprises a pacing therapy, and adjusting the cardiac electrical therapy comprises adjusting an atrioventricular (A-V) delay of the pacing therapy.

11. The method of claim 1, wherein the cardiac electrical therapy comprises a pacing therapy, and adjusting the cardiac electrical therapy comprises adjusting a pacing rate of the pacing therapy.

12. The method of claim 1, wherein the cardiac electrical therapy comprises a pacing therapy, and adjusting the cardiac electrical therapy comprises adjusting a pacing site for the pacing therapy.

13. The method of claim 1, wherein the cardiac electrical therapy comprises a resynchronization therapy delivered to the heart.

14. The method of claim 1, wherein the cardiac electrical therapy comprises a bi-ventricular pacing therapy, and adjusting the cardiac electrical therapy comprises adjusting an inter-ventricular delay or an atrioventricular (A-V) delay of the bi-ventricular pacing therapy.

15. The method of claim 1, wherein processes of claim 1 are repeated until a determination is made that the adjustment in the cardiac electrical therapy decreased cardiac efficiency based on the calculated change in the cardiac efficiency parameter.

16. The method of claim 15, further comprising selecting a previously adjusted cardiac electrical therapy for delivery if the adjustment of the cardiac electrical therapy was determined to decrease cardiac efficiency.

17. A system for improving cardiac efficiency, comprising:
means for measuring, patient-internally in at least one of a coronary vein and the great cardiac vein of the patient's heart, oxygen saturation indicative of oxygen usage of myocardial tissue of the heart;
means for measuring cardiac stroke volume;
means for calculating a cardiac efficiency parameter based on the measured oxygen saturation and the measured stroke volume;
means for adjusting a cardiac electrical therapy to cause a change of the measured oxygen saturation;
means for calculating a change in the cardiac efficiency parameter resulting from the cardiac electrical therapy adjustment;
means for determining whether the adjustment of the cardiac electrical therapy decreased or increased cardiac efficiency based on the calculated change in the cardiac efficiency parameter; and
means for selecting the adjusted cardiac electrical therapy for delivery if the adjustment of the cardiac electrical therapy was determined to increase cardiac efficiency.

18. The system of claim 17, wherein means for determining whether the adjustment of the cardiac electrical therapy decreased or increased cardiac efficiency comprises means for determining whether oxygen saturation increased or decreased from the adjustment of the cardiac electrical therapy, the therapy adjustment being determined to increase cardiac efficiency if higher oxygen saturation is measured after the therapy adjustment and the therapy adjustment being determined to decrease cardiac efficiency if lower oxygen saturation is measured after the therapy adjustment.

19. The system of claim 17, wherein the means for calculating the change in cardiac efficiency comprises means for computing the patient's cardiac efficiency using the measured stroke volume.

* * * * *